(12) United States Patent
Wilssens

(10) Patent No.: US 6,505,522 B1
(45) Date of Patent: Jan. 14, 2003

(54) APPARATUS AND METHOD FOR MEASURING THE PRESSURE DISTRIBUTION GENERATED BY A THREE-DIMENSIONAL OBJECT

(75) Inventor: Jean-Pierre Wilssens, Beveren (BE)

(73) Assignee: RS Scan, Beveren (BE)

(*) Notice: Subject to any disclaimer, the term of this patent is extended or adjusted under 35 U.S.C. 154(b) by 0 days.

(21) Appl. No.: 09/185,197

(22) Filed: Nov. 3, 1998

(51) Int. Cl.$^7$ ................................................ G01D 9/00
(52) U.S. Cl. .................................................. 73/862.51
(58) Field of Search ..................... 73/862.046, 862.041, 73/862.042, 862.044, 862.045, 862.51, 777, 862.4, 172, 865.4, 865.7

(56) References Cited

U.S. PATENT DOCUMENTS

| | | | | |
|---|---|---|---|---|
| 4,695,963 A | * | 9/1987 | Sagisawa et al. ............ 364/513 |
| 4,906,192 A | * | 3/1990 | Smithard et al. ............ 434/253 |
| 5,323,650 A | * | 6/1994 | Fullen et al. .................. 73/172 |
| 5,505,072 A | | 4/1996 | Oreper ......................... 73/4 R |
| 5,736,656 A | | 4/1998 | Fullen et al. ............... 73/865.4 |
| 5,952,585 A | * | 9/1999 | Trantzas et al. ........ 73/862.046 |

FOREIGN PATENT DOCUMENTS

| | | | |
|---|---|---|---|
| GB | 2256933 | 12/1992 | ............ A61B/5/103 |
| WO | WO9305711 | 4/1993 | ............ A61B/5/103 |

OTHER PUBLICATIONS

IEEE Transactions on Rehabilitation Engineering, vol. 5, No. 5, Dec. 1997, "Piezo–Dynamometric Platform for a More Complete Analysis of Foot–to–Floor Interaction," C. Giacomozzi and V. Macellari.

* cited by examiner

*Primary Examiner*—William Oen
(74) *Attorney, Agent, or Firm*—Jack V. Musgrove

(57) ABSTRACT

A self-calibrating apparatus and a self-calibrating method for measuring the pressure distribution generated by a three-dimensional object, is described which includes a plurality of first non-linear force sensors arranged in an array; and a second force sensing device (3) having a linear or linearisable output for measuring the total force applied to the first force sensors. The first sensors are dynamically calibrated based on the results of the comparison. The three-dimensional object may be a human foot and the apparatus and method amy be sued for fitting shoes or for determining irregularities or ailments of the human foot or leg.

20 Claims, 4 Drawing Sheets

| sensor output value | calibration factor |
|---|---|
| 1 | 1,1 |
| 2 | 0,9 |
| 3 | 0,85 |
| 4 | 1,5 |
| 5 | 2,3 |
| 6 | 1,0 |
| 7 | 0,58 |
| 8 | 0,7 |
| ǀ | ǀ |
| etc | etc |
*Fig. 4*
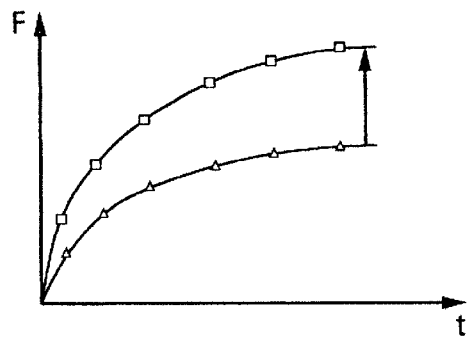
*Fig. 5A*
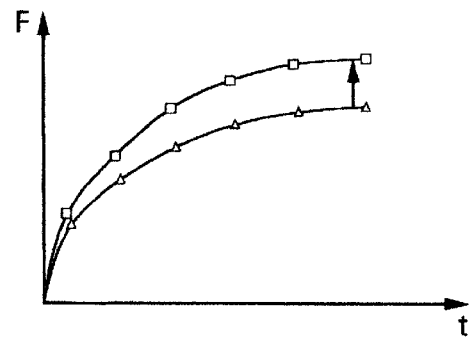
*Fig. 5B*
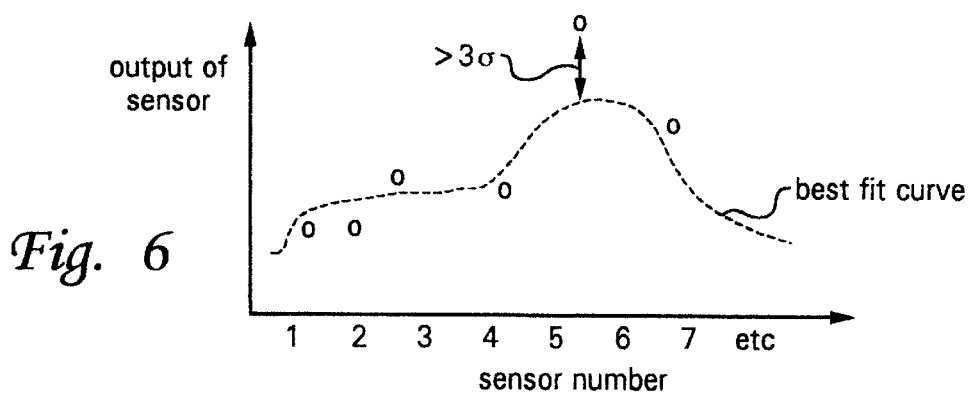
*Fig. 6*

APPARATUS AND METHOD FOR MEASURING THE PRESSURE DISTRIBUTION GENERATED BY A THREE-DIMENSIONAL OBJECT

The present invention relates to an apparatus and a method of measuring the pressure distribution generated by a three-dimensional object, in particular the feet of humans or animals. The present invention is particularly useful in the diagnosis of leg and foot abnormalities and in the selection and design of foot wear.

TECHNICAL BACKGROUND

Several devices have been designed to measure forces applied by the foot. These include devices for measuring applied forces that are attached to the foot during walking or running, for measuring peak pressure, for measuring the total force applied by the foot, and for measuring forces applied by certain areas of the foot for various purposes. Other devices employ a stationary foot sensor pad and are suited for use in a laboratory or hospital.

Conventional foot force measurement devices function to convert mechanical force into a suitable electrical signal. The types of sensors used include pneumatic or hydraulic fluid activated switches, strain gauge sensors that respond to mechanical deformation, single direct electronic force sensors or multiple direct electronic force sensors.

Pneumatic and hydraulic sensors are prone to produce inaccurate readings because changes in internal pressure are not necessarily proportional to change in forces. One way to construct an accurate fluid sensor is to use rigid plates which limit the applied force to a constant area of fluid contact. In such sensors, the fluid pressure is proportional to the applied force. However, these sensors are disadvantageous due their bulkiness and weight.

The sensors which measure mechanical deformation of structural elements supporting the wearer's foot by use of electrical wire or ribbon type strain gauges accurately measure weight, but they are also disadvantageous because of their bulk and weight.

In direct electronic force sensor devices, the applied pressure compresses a partially conductive material (carbon granules) and thereby reduces its electrical resistance. A force sensor based on this concept can be constructed by forming thin electrodes on two plastic films and then covering the electrodes with a thin layer of suitable partially conductive material. When the two coated films are positioned so that the two layers of partially conductive material are in contact, the electrical resistance through the sensor from electrode to electrode varies inversely with a compressing force on the sensor. This is because as the coating is pressed with greater force, the electrical current path becomes broader due to increased area of contact. This effect occurs with any conductive material, but materials useful as active elements in practical force sensors must have a relatively high electrical resistance. Such thin film electronic force sensors have the advantages of simplicity, compactness, and light weight, but the disadvantage that they only provide relative indications of pressure applied.

In multiple direct electronic force sensors the sensors may be regularly spaced. Since the relative position of each sensor is fixed, a mathematical description of the location of each sensor can easily be made part of a permanent computer database. These sensor arrays are very thin and very light weight, but they cannot conform to a compound curved surface without wrinkling. Such wrinkled or folded thin film sensor arrays may produce erroneous results. A wrinkled sensor array may produce an electrical signal from the wrinkle alone. Folding or wrinkling also subjects the sensor array to severe fatigue stress, which can lead to early and sudden failure.

A practical sensor array preferably includes a large number of individual force sensors. The problem of electrically connecting this number of individual sensors to data acquisition circuitry is a significant one. Preferably a two-vector array of rows and columns is provided with a top electrode of all sensors in each column commonly connected and a bottom electrode of all the sensors in each row likewise commonly connected.

Insole force sensor arrays are described in U.S. 5,408,873 and U.S. 5,678,448. In addition, alternative apparatuses makes use of a flat pressure sensor array onto which the person places his or her foot as disclosed, for example, in U.S. 5,659,395. Typically the pressure sensor array may be provided by a large number of resistive pressure sensors. This flat plate arrangement has the advantage that there is no bending or folding of the pressure pad which makes the design of the pressure sensors somewhat simpler and allows a high density and a high number of individual pressure sensors to be included within the pressure pad.

Independent of whether an insole pressure device is used or a flat plate, the use of resistive pressure sensors is convenient and provides a light weight apparatus. However, the major disadvantage of resistive pressure sensors is that they are not absolutely calibrated but rather provide relative pressure values. In addition it is possible, through use, that pressure sensors in one area of a pressure path may alter their response characteristic with time. Calibrating or re-calibrating the multitude of pressure sensors in a pressure pad is not only time consuming but also difficult to carry out exactly. As the pressure pad is not absolutely rigid, it is difficult to apply a uniform pressure to individual or groups of sensors.

It is an object to the present invention to provide a pressure distribution sensing apparatus and method for sensing the pressure distribution of a three-dimensional object which avoids or reduces the problems of calibration or re-calibration of pressure known pressure pads.

It is a further object of the present invention to provide a force sensing apparatus which is light in weight and is convenient to use for determining the pressure distribution generated by a three-dimensional object.

SUMMARY OF THE INVENTION

The present invention includes a self-calibrating apparatus for measuring the pressure distribution generated by a three-dimensional object, comprising: a plurality of first non-linear force sensors arranged in an array; and a second force sensing device having a linear or linearisable output for measuring the total force applied to the first force sensors.

The present invention includes an apparatus for measuring the pressure distribution generated by a three-dimensional object, comprising: a substantially rigid plate; a plurality of first force sensors arranged in an array, the array of first force sensors being arranged to be on one side of the plate; and a second force sensing device for measuring the total force applied to the plate.

The present invention may also include a method of measuring the pressure distribution generated by a three-dimensional object, comprising the steps of: providing a plurality of first non-linear force sensors arranged in an array; providing a second force sensing device having a linear or linearisable output for measuring the total force applied to the first force sensors; obtaining readings of the force on each sensor of the array of first pressure sensors; adding together the readings from all the first force sensors in the array and comparing this result with the output of the second force sensing device.

The present invention may also include a method of measuring the pressure distribution generated by a three-dimensional object, comprising the steps of: providing a substantially rigid plate; providing a plurality of first force sensors arranged in an array, the array being arranged to be on one side of the plate; providing a second force sensing device for measuring the total force applied to the plate; scanning the array of first force sensors to obtain readings of the force on each sensor; adding together the readings from all the first force sensors in the array and comparing this result with the output of the second force sensing device.

The present invention may provide the advantage that the relative pressure measurements generated by a resistive pressure pad may be continuously and dynamically calibrated by means of a second force sensing device. The second force sensing device is preferably one which is easily calibrated, is linear in its output and is stable. Preferred second sensor devices are an array of strain gauge force sensing devices, piezo-resistive or piezo-electric sensing devices. Preferably the second sensors are read out in parallel. The most preferred second sensing device is one or more piezoelectric sensors. All or any of the apparatus and methods of the present invention may assist in fitting shoes and in gaining physiological data about the human foot or leg. All or any of the apparatus according to the present invention may be provided as a self-contained system.

The dependent claims define individual and separate embodiments of the present invention. The present invention will now be described with respect to the following drawings.

BRIEF DESCRIPTION OF THE DRAWINGS

FIG. 4 is a representation of a look-up table for calibration factors in accordance with an embodiment of the present invention.

FIGS. 5A and 5B show representative outputs of the force sensors of the present invention, before and after a first calibration.

FIG. 6 shows a representation of the outputs from one row or column of force sensors.

DESCRIPTION OF THE ILLUSTRATIVE EMBODIMENTS

The present invention will be described in the following mainly with respect to a device for measuring the pressure and/or force on the feet of human beings or animals during walking, running, jumping or standing. The invention is not limited thereto but may be used for the measurement of the pressure distribution generated by any three-dimensional object. Further, the present invention will be described mainly with respect to the use of an array of resistive force sensors, but the present invention is not limited thereto. Alternative force sensing devices may be used, for instance capacitive or inductive force sensing devices. Further, the present invention will be described mainly with respect to the use of piezo-electric sensors as the second sensing device for measuring the total force on the intermediate plate. The present invention is not limited thereto but includes other force or pressure sensing devices, in particular strain gauge and piezo-resistive force sensing devices with analogue or digital readouts.

Figure 1:
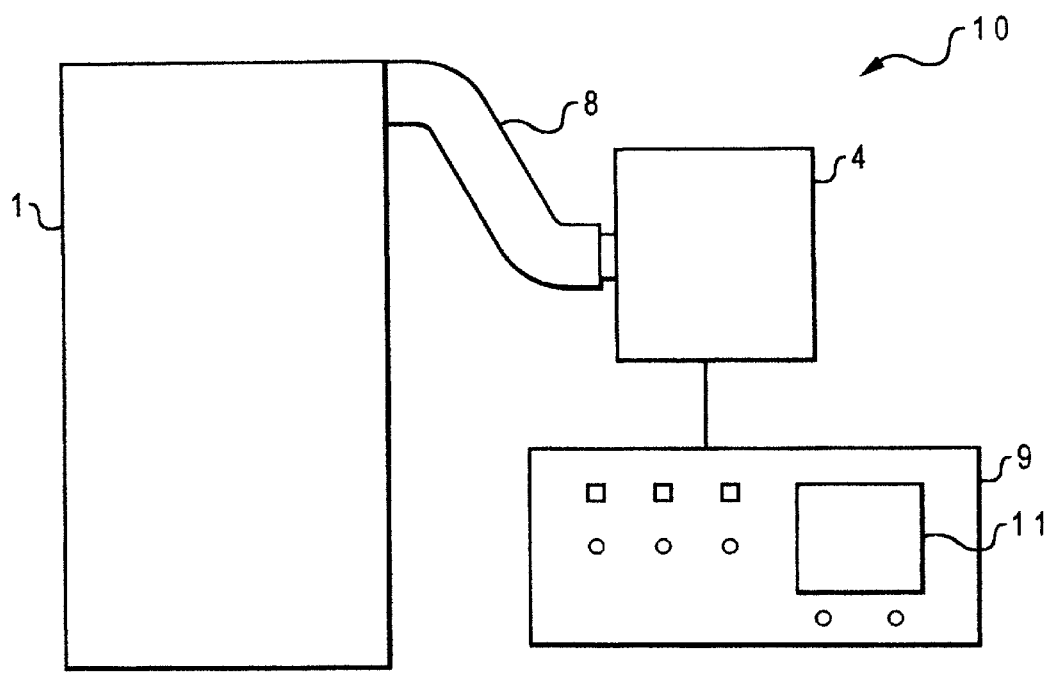
FIG. 1 is a schematic representation of a pressure distribution sensing apparatus in accordance with a first embodiment of the present invention.

FIG. 1 is a schematic representation of a first embodiment of a pressure distribution sensing apparatus 10 in accordance with the present invention. It includes a substantially flat pressure sensing plate 1 which includes force sensing devices which will be described later, a means 8 for transmitting the individual values outputted by the force sensors in plate 1 representing the force applied to them to suitable read out electronics 4 and processing and storage electronics 9 including an optional display 11. Transmission means 8 may include cables, optical, e.g. infrared, microwave transmission devices or similar, i.e. the present invention includes both a direct connection between plate 1 and read out electronics 4 via cables as well as remote connection via any form of electromagnetic radiation communication method.

Figure 2:
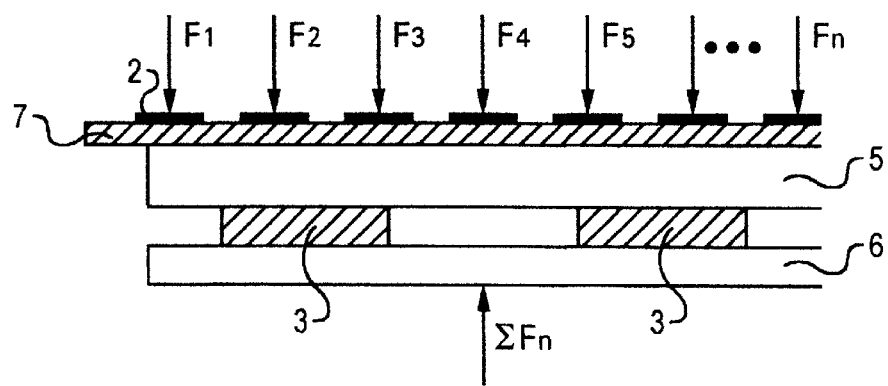
FIG. 2 is a schematic cross-sectional representation of a pressure plate in accordance with an embodiment of the present invention.
Figure 3:
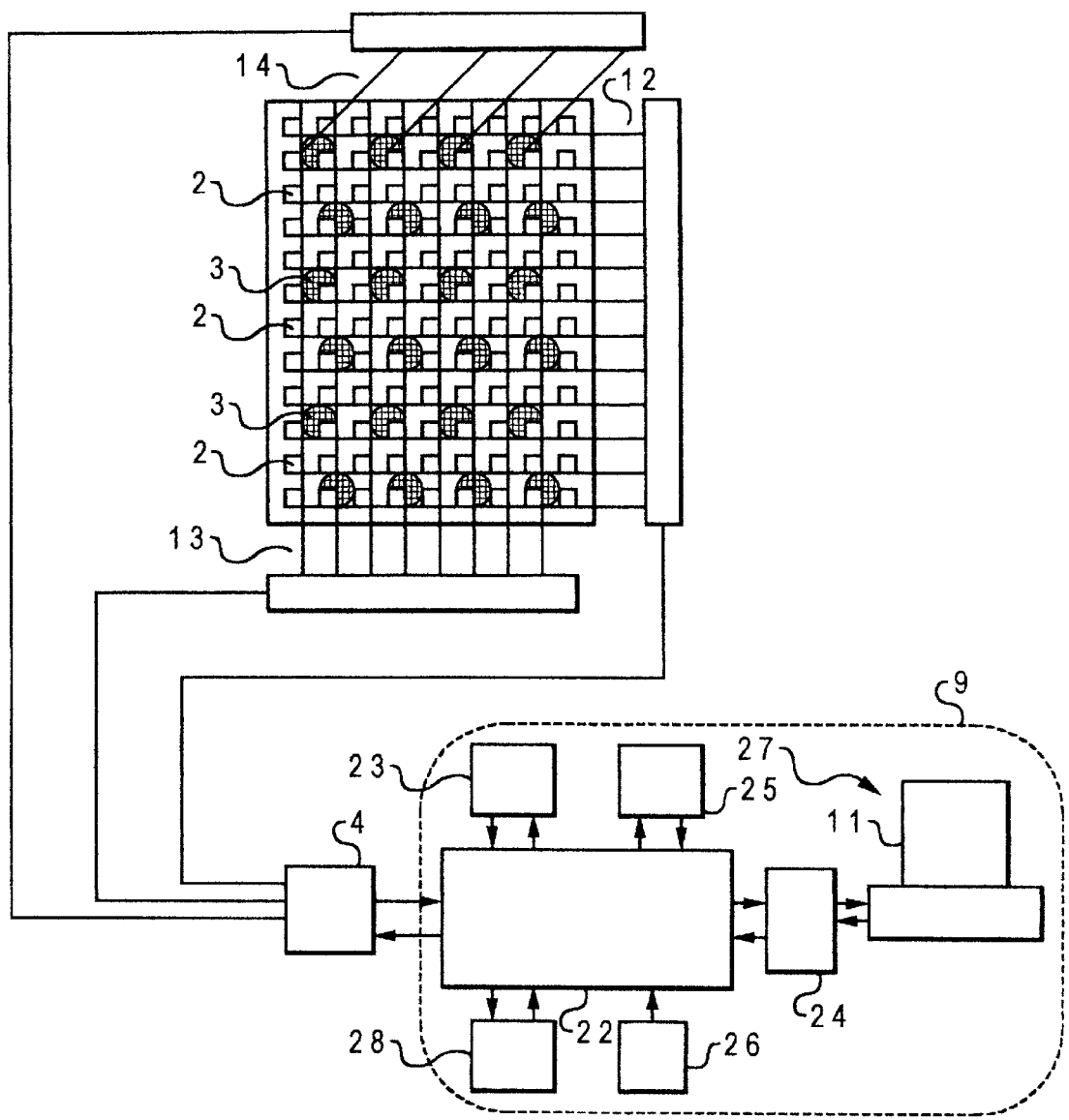
FIG. 3 is a is a further schematic representation of the pressure distribution sensing apparatus in accordance with the first embodiment of the present invention.

FIG. 2 is a schematic detailed cross-sectional representation of one embodiment of the pressure sensing plate 1 shown in FIG. 1. FIG. 3 includes a schematic top view of one arrangement of sensors 2, 3 in accordance with the present invention. Sensing plate 1 includes a plurality of impedance sensing devices 2 arranged in a regular two dimensional array. Sensors 2 are preferably resistive sensors but may also be capacitive or inductive sensors. Connections 12, 13 are provided for measuring the resistance of each individual sensing device 2 and outputting this as a signal. Resistive sensors generally have a non-linear force/resistance characteristic. There may be several thousand resistive sensing devices 2 arranged in an array of rows and columns or a similar organised structure and the sensors 2 are preferably distributed evenly over plate 1. The position of each sensor 2 on the plate 1 is preferably known and this position is stored in the electronics 9 and associated with the specific sensor 2. Force sensing devices 2 may be formed from a single sheet of resistive material 7 and covered by a suitable outer thin flexible layer (not shown). Underneath layer 7, a substantially rigid plate 5 is provided which may be several millimetres thick and made of a suitable rigid material such as steel or rigid plastic. One or more second force sensing devices 3 are provided which co-operate with plate 5 so that the total downward force on plate 5 is equal to the sum of the outputs of the second sensors 3. The positions of the second sensing devices 3 relative to plate 1 are optionally also stored in the electronics 9. Optionally, a further support plate 6 may be provided on which the second force sensing devices 3 are located.

Plate 1 is placed on a suitable flat object such as a floor in such a way that when a three-dimensional object is placed on the surface of plate 1 the local pressure exerted by the object influences the output of each of the plurality of first force sensing devices 2. As the total force on the plate 1 is measured by the sum of the outputs of the one or more second force sensing devices 3, the sum total of all the outputs of the force sensing devices 2 should equal the sum total of the outputs of the second sensing devices 3. Any difference in these totals is an indication that the calibration of the first force sensors 2 is incorrect. Typically, fewer second force sensing devices 3 are provided than first sensors 2, e.g. one centrally placed sensor 3 up to several hundred or more may be provided. Sensors 3 are preferably distributed equally over plate 1. Second force sensing devices 3 may be considerably larger in diameter than the force sensing devices 2 and are preferably of the type which can be easily calibrated, provide a linear output or a linearisable output with respect to the force applied and are stable over time. By linearisable output is meant that the second type of force sensor 3 may have a non-linear output but this is sufficiently reproducible that it can be linearised by suitable electronics either in the sensor itself or incorporated in the measuring electronics 4, 9. Preferred second force sensing devices 3 are piezo-electric sensors supplied, for instance, by Kistler of Switzerland.

As best shown in FIG. 3 the array of first sensors 2 are connected to the scanning electronics 4 by means of connecting lines 12, 13. It is possible to read out all the sensors 2 in parallel, however for large size arrays (10,000 sensors or more) it is more practical to read out the sensors 2 in sequence using addressing lines 12, 13 with which each one of the sensors 2 may be addressed sequentially by placing a voltage on each of the respective lines 12, 13 which intersect at the desired sensor 2. The ratio of applied voltage to current flowing provides a measure of the resistance of the sensor 2 and hence an indication of the applied force. The analogue result (resistance) derived from each sensor 2 is converted to digital signals in scanning means 4. Second sensors 3 are preferably read out in parallel which requires a connection 14 to each sensor 3 (not all connections are shown in FIG. 3 to avoid confusion). It is preferable to read out all second sensors 3 in parallel so that the sum of all outputs of the sensors 3 is available from one instant of time. This means that the instantaneous force applied to the plate 1 can be calculated from the sum of the read outs of all sensors 3 at one instant. It is preferred if the rate of reading out sensors 3 is high, e.g. several thousand times per second so that dynamic changes of foot loading on plate 1 can be tracked accurately. The scanning rate of the array of first resistive sensors 2 may be lower, e.g. a complete scan of all sensors 2 may be completed several hundred times per second. As the scan of the array of first sensors 2 is sequential, the picture of the pressure distribution is not instantaneous but is spread over the time for one scan. This time period is preferably still very small, i.e. of the order of thousandths or hundredths of a second so that the pressure distribution on plate 1 is effectively "frozen" over one scan of sensors 2.

Referring now to FIG. 3, which only shows one possible implementation of the present invention, the array of force sensors 2 is connected to measuring electronics 4, 9, which contains scanning circuitry 4 controlled by a central processing unit (CPU) 22. CPU 22 executes software routines stored in a read-only memory (ROM) 23 during system boot up and thereafter executes software programs stored in a random access memory (RAM) 25. An interface 24 is used to upload data stored in RAM 25 to an external personal computer (PC) 27 and to down-load operational data and software programs from the PC 27 to RAM 25. A clock 26 provides time and date information to CPU 22. Non-volatile read-write memory 28 may also be provided to store data which is to survive power down and boot up.

The resistance of each force sensor 2 of the array of force sensors 2 is inversely proportional to the applied force and the response is non-linear and may vary between individual sensors 2 due to unavoidable manufacturing variances. To provide some adjustment because of these manufacturing tolerances and non-linear effects, a two-vector data array may be stored within the RAM 25 previously loaded into non-volatile memory 28 by use of a PC and other suitable test equipment. In this array, a first vector applies to each sensor 2, and a second vector applies to each possible resistance value of a particular sensor 2. Contained in each storage location within the data array is the appropriate output value for that combination of sensor 2 and resistance value. The information stored in the data array for a particular sensor 2 currently being evaluated is used to translate the measured characteristic (e.g. resistance) of the individual sensor 2 to a value representing the force being placed on the sensor 2. Each sensor 2 is scanned in turn, its value translated, and each translated value is added to the value representing the total force measured by the array of force sensors 2. Following a single scan of the complete array of force sensors 2, the total force on the array force of sensors 2 is available as well as the force value from each sensor 2 which may be used to create a graphical image of the pressure distribution on the display 11. The total force value computed from the sum of all the measured and translated outputs of sensors 2 is compared with the sum of the values obtained from the second force sensors 3. Any difference between these two sums indicates that a further correction or calibration of the force sensors 2 is required.

The method of using the pressure distribution sensing apparatus 10 of FIGS. 1–3 will now be described. Initially, the second pressure sensing devices 3 may be calibrated. This may be done individually before placing the sensors 3 in the device 10 and/or by applying a known weight to pressure plate 1, e.g. 50 kilograms, with the sensors 3 in place. As the sum total of the signal outputs of the second pressure sensing devices 3 should equal the total force on plate 1, the sum total of the outputs of the second sensory devices 3 can be calibrated against the known weight. Smaller weights may be distributed over the surface of plate 1 to obtain further information about the calibration of both the first and second sensors 2, 3 however this is not essential. The force sensors 2 may have a non-linear output and measuring electronics 4, 9 includes means for converting the non-linear output of these senses into accurate force readings. This may be done by multiplying the output of each sensor 2 obtained after it has been translated by a factor which converts (corrects) the translated output into an absolute force reading. The necessary calibration factors may be included in a separate look-up table as shown schematically in FIG. 4. The present invention is not limited to look-up tables and a skilled person is aware of alternative methods of linearising the output of a force sensor. The look-up table includes a calibration factor for each of a plurality of output values of each sensor 2. These calibration values are used to correct the force values determined from the two vector array which is used to translate the measured characteristic of each sensor 2. The more calibration factor values are stored in the look-up table, the more accurate is the conversion of the measured outputs. Initially the calibration factor values may all be set to one specific value or to what are considered to be suitable values. The apparatus 10 in accordance with the present invention is selfcalibrating so that these initial values are not of great importance. A dynamic load is now placed upon the plate 1 and the sum of all the translated outputs of the sensors 2 is compared with the sum of all the outputs of sensors 3 at different times. FIG. 5A is a schematic representation of a loading on plate 1 in which each point on the lower curve is the sum total of all the translated outputs from the array of sensors 2 in one scan and each point on the upper curve is the sum total of the outputs from the force sensing device 3. Initially as shown in FIG. 5A, the translation values in the two-vector data array of the force sensors 2 are not accurate and there is a difference between the sum total of the outputs from sensors 2 and sensors 3. The ratio of these sum totals of the outputs provides a calibration factor for the sensors 2. This calibration value is available only for one force i.e. the average force on plate 1 during that scan. In accordance with one embodiment of the present invention the translation values for this particular force in the two-vector data array for all the sensors 2 are multiplied by the determined calibration factor which is stored in the look-up table. As the calibration factor for each new force is determined, the look-up table is updated for this particular force with the determined calibration factor and all the translation values in the two-vector array for this force are multiplied by the calibration factor. Hence, as the load on plate 1 varies, further calibration factors for other forces are determined in this way. Note, that as the sum total of the translated outputs of the sensors 2 in one complete scan is made up of different forces, the calibration factors determined by the above method after one load cycle of plate 1 are not perfect. As shown in FIG. 5B, after one load cycle, the gap between the two curves is smaller but not eliminated. However, with more load cycles, the approximations become more and more accurate until the final output displayed on the display 11 is absolute pressure values and not relative ones.

This process of self-calibration is dynamic, i.e. if the non-linear characteristic of the sensors 2 alters because of change of temperature, for instance, these changes will be detected by differences between the sum totals of the translated and corrected outputs of sensors 2 of the array and the sum totals of the outputs of sensors 3 and appropriate changes may be made to the calibration factors. At the end of a significant number of load cycles the calibration factors in the look-up table are preferably stored in non-volatile memory for use as the initial values at the start of the next test run.

The above description includes the use of a separate calibration or correction look-up table which is used to correct the force estimates obtained from the two-vector translation array. However, the present invention is not limited thereto, for instance, the values in the two-vector array could be dynamically corrected based on the determined calibration factor thus eliminating the look-up table. One disadvantage of the above embodiment of the present invention is that the calibration factors for sensors 2 are global, i.e. they are applied to all the sensors 2 uniformly rather than providing individual calibration factors for each individual sensor 2. The present invention also includes providing calibration factors for individual sensor 2 or groups of sensors 2. One way of providing individual calibration factors will be described with respect to FIG. 6. In order to provide individual calibration factors for each sensor 2 it is necessary to have a look-up table for each sensor 2, i.e. to provide a second two-vector array in which one vector points to the sensor 2 to be evaluated and the other vector points to the output value of the sensor 2. The data located at this address in the array provides the calibration factor for the sensor. Generally, if the outputs of one row or one column of the array of sensors 2 are analysed (FIG. 6) they will provide a relatively smooth function. This may require that there are no very sharp edges on the object which is being measured. This is generally true for the feet of humans. It is generally possible to fit the individual output values of sensors 2 obtained from one row or one column to a smooth curve using a suitable curve fitting algorithm. For instance, the output of one row or one column may be fitted with a third order polynomial using a least squares curve fitting technique. The difference between the calculated curve and each individual translated sensor output may be determined by subtraction and these error values converted into a standard deviation a by a suitable technique, e.g. least squares. The deviation between each individual output in the row or column and the best fit curve is then compared with the standard deviation $\sigma$, and any output which shows a significant deviation, i.e. greater than 3 $\sigma$, indicates that the calibration factor for this sensor 2 and for this force must be altered. Hence, the calibration factor for that force is amended in the second two-vector array for that particular sensor. The number of times a sensor 2 has values which exceed the standard deviation $\sigma$ by a significant amount may also be stored which may give an indication of a sensor 2 which has erratic behaviour, e.g. a poor contact.

Figure 7:
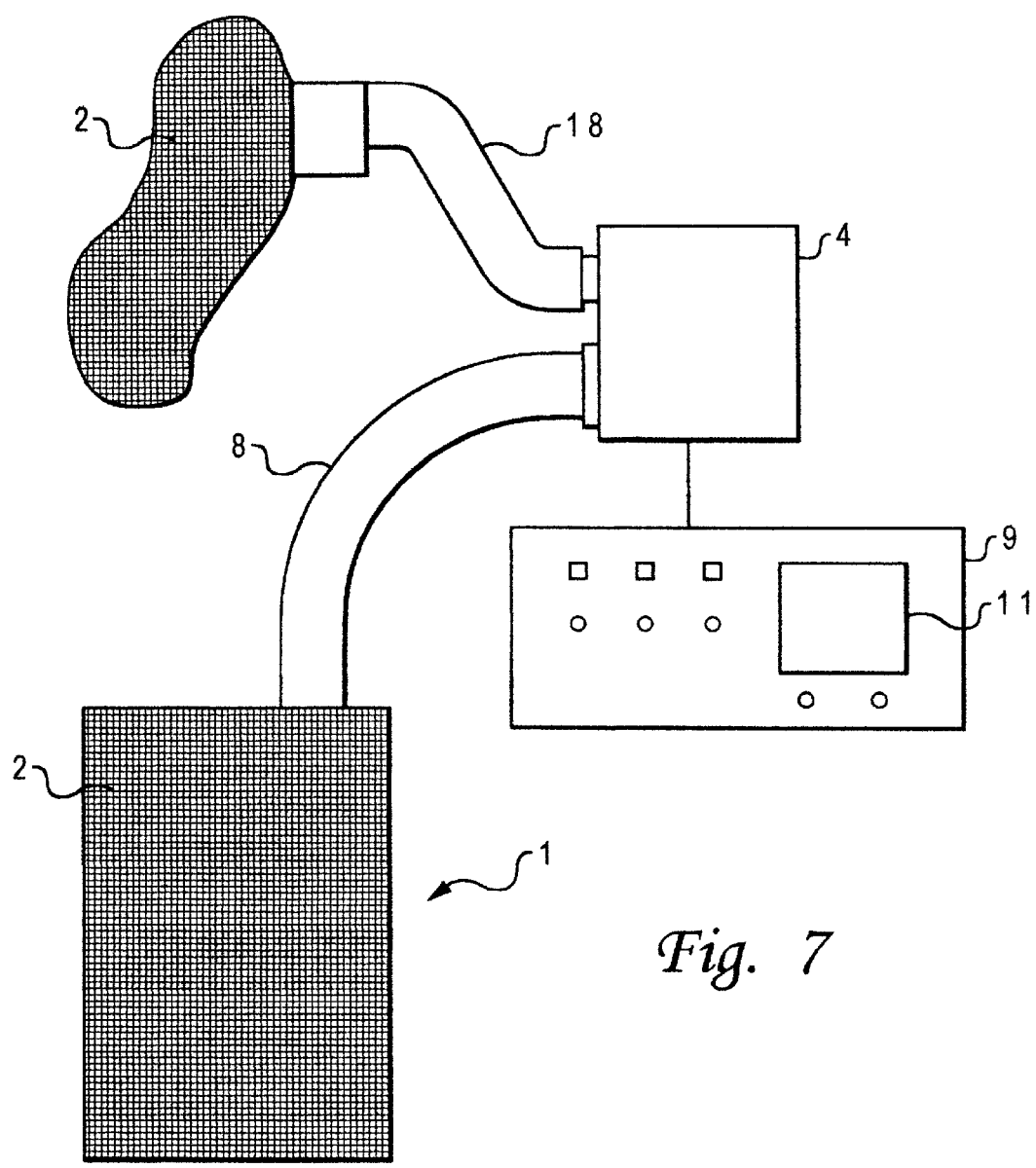
FIG. 7 is a schematic representation of a pressure distribution sensing apparatus in accordance with a second embodiment of the present invention

FIG. 7 is a schematic representation of a second embodiment of a pressure distribution measuring apparatus 10 in accordance with the present invention. The major distinction between the second and first embodiments of the present invention is that the array of sensors 2 in accordance with the second embodiment need not be included within pressure plate 1 but may be included in an insole array. The array of sensors 2 is positioned relative to a user's foot thus allowing the measurement of the forces applied by the foot while the user is standing, walking, jumping or running. Such an array of non-linear resistive elements is disclosed, for instance, in U.S. 5,678,448. The sensors 2 of the insole array may be non-linear resistive sensors as described for the first embodiment. Preferably, there is an interconnection means 18 between the insole array of sensors 2 and the measuring electronics 4, 9 which does not impede a movement of the user. For instance, a remote transmission method may be used such as infrared or microwave transmission.

The operation of the measuring apparatus 10 in accordance with the second embodiment is, in principal, the same as for the first embodiment. The person attaches the insole array to his or her foot, e.g. by putting on a special shoe in which the insole array is located. The person then places the shoe on the pressure plate, e.g. by standing walking or running on the plate 1. The second sensors 3 measure the total force applied to plate 1 at any instant. The insole array of sensors 2 is read out in a sequential fashion whereas the second sensing devices 3 associated with pressure plate 1 are read out in parallel at high frequency. Pressure plate 1 for the second embodiment can be identical to the pressure plate 1 for the first embodiment except for the fact that there need be no connection between the arrays of pressure sensors 2 associated with plate 1 and the measuring electronics 4, 9. Instead, the sensors 2 of the insole array may be connected to the measuring electronics 4, 9 directly. The self-calibrating procedure described with respect to the first embodiment may also be applied to the second embodiment so that the sum total of the translated outputs from the sensors 2 of the insole array is compared with the total output of the second sensing devices 3 after each scan of the complete insole array. Any difference between these two is compensated for by amending the calibration factors in the look-up table or the second two-vector data array as has been described with respect to the first embodiment.

While the invention has been shown and described with reference to preferred embodiments, it will be understood by those skilled in the art that various changes or modifications in form and detail may be made without departing from the scope and spirit of this invention as defined in the attached claims.

What we claim is:

1. A self-calibrating apparatus for measuring a pressure distribution generated by a three-dimensional object, comprising:
   a plurality of first non-linear force sensors arranged in an array, the measured pressure distribution being based on output of the first non-linear sensors;
   a second force sensing device having a linear or linearisable output for measuring a total force applied to the first force sensors, and
   means for calibrating the first non-linear force sensors based on the output of the first non-linear sensors and the second force sensing device.

2. The apparatus according to claim 1, further comprising a device for calculating the total force applied to all the first sensors in the array and to calculate the total force applied to the second sensing device and for comparing the two results.

3. The apparatus according to claim 2, wherein the means for calibrating comprises a device for calibrating the first force sensors depending on the result of the comparison.

4. The apparatus according to claim 1, wherein the array of first sensors is included in one pressure sensing device and the second sensing device is included in a second pressure sensing device.

5. The apparatus according to claim 1, further comprising a device for determining an individual calibration factor of each first sensor.

6. The apparatus according to claim 1, wherein the three dimensional object is a human foot.

7. A self-calibrating apparatus for measuring a pressure distribution generated by a three-dimensional object, comprising:
   a substantially rigid plate;
   a plurality of first force sensors arranged in an array, the array of first force sensors being arranged to be on one side of the plate;
   a second force sensing device for measuring a total force applied to the plate, and
   means for calibrating the first non-linear force sensors based on the output of the first non-linear sensors and the second force sensing device.

8. The apparatus according to claim 7, further comprising a device for calculating the total force applied to all the first sensors in the array and to calculate the total force applied to the second sensing device and for comparing the two results.

9. The apparatus according to claim 8, wherein the means for calibrating comprises a device for calibrating the first force sensors depending on the result of the comparison.

10. The apparatus according to claim 7, wherein the array of first sensors is included in one pressure sensing device and the second sensing device is included in a second pressure sensing device.

11. The apparatus according to claim 7, further comprising a device for determining an individual calibration factor of each first sensor.

12. The apparatus according to claim 7, wherein the three dimensional object is a human foot.

13. A method of measuring a pressure distribution generated by a three-dimensional object, comprising the steps of:
   providing a plurality of first non-linear force sensors arranged in an array, the measured pressure distribution being based on output of the first non-linear sensors;
   providing a second force sensing device having a linear or linearisable output for measuring a total force applied to the first force sensors;
   obtaining readings of the force on each sensor of the array of first pressure sensors;
   adding together the readings from all the first force sensors in the array;
   comparing this result with the output of the second force sensing device, and calibrating the first non-linear force sensors based on the result of the comparison.

14. The method according to claim 13, further comprising the step of calibrating the first force sensors depending on the result of the comparison.

15. The method according to claim 13, further comprising the step of determining an individual calibration factor for each first sensor.

16. The method according to claim 13, wherein the three dimensional object is a human foot.

17. A method of measuring a pressure distribution generated by a three-dimensional object, comprising the steps of:
   providing a substantially rigid plate;
   providing a plurality of first force sensors arranged in an array, the array being arranged to be on one side of the plate;
   providing a second force sensing device for measuring a total force applied to the plate;
   scanning the array of first force sensors to obtain readings of the force on each sensor;
   adding together the readings from all the first force sensors in the array,
   comparing this result with the output of the second force sensing device, and calibrating the first non-linear force sensors based on the result of the comparison.

18. The method according to claim 17, further comprising the step of calibrating the first force sensors depending on the result of the comparison.

19. The method according to claim 17, further comprising the step of determining an individual calibration factor for each first sensor.

20. The method according to claim 17, wherein the three dimensional object is a human foot.

* * * * *